United States Patent [19]

Burke

[11] Patent Number: 5,250,726
[45] Date of Patent: Oct. 5, 1993

[54] PROCESS FOR THE PREPARATION OF 3-PENTENOIC ACID FROM BUTADIENE

[75] Inventor: Patrick M. Burke, Wilmington, Del.

[73] Assignee: E. I. Du Pont de Nemours and Company, Wilmington, Del.

[21] Appl. No.: 933,942

[22] Filed: Aug. 24, 1992

[51] Int. Cl.⁵ .............................................. C07C 51/14
[52] U.S. Cl. .................................................... 562/522
[58] Field of Search ................................ 562/522, 545

[56] References Cited

U.S. PATENT DOCUMENTS 5,145,995  9/1992  Burke ................................. 562/522
5,149,868  9/1992  Drent ................................. 562/522

Primary Examiner—Arthur C. Prescott

[57] ABSTRACT

Preparation of 3-pentenoic acid by reacting butadiene and carbon monoxide using a rhodium catalyst and a sulfonic acid catalyst in water and a carboxylic acid solvent.

7 Claims, No Drawings

PROCESS FOR THE PREPARATION OF 3-PENTENOIC ACID FROM BUTADIENE

FIELD OF THE INVENTION

This invention relates to an improved process for the rhodium-catalyzed hydrocarboxylation of butadiene to form 3-pentenoic acid.

BACKGROUND OF THE INVENTION

In U.S. Pat. No. 4,690,912, Paulik et al. disclose a bromide- or iodide-promoted rhodium catalyst system for the carbonylation of carbonylatable reactants. In Example 55, butadiene is converted to greater than 79 wt. % $C_5$ carboxylic acids.

In U.S. Pat. No. 4,622,423, Burke discloses the preparation of 3-pentenoic acid by hydrocarboxylating butadiene with carbon monoxide and water in the presence of a rhodium-containing catalyst, an iodide promoter and certain halocarbon solvents. Methylene chloride is the preferred solvent; acetic acid in aqueous solution is said to be undesirable.

In U.S. Pat. No. 4,788,334, Burke discloses a process for the hydrocarboxylation of linear olefinically unsaturated esters and terminally unsaturated alkenes having 4 to 16 carbon atoms to form a mixture which contains an increased amount of the linear carboxylic acid. The reaction mixture comprises the ester or the terminally unsaturated alkene, carbon monoxide, water, a halocarbon or aromatic solvent, a rhodium catalyst, an iodide promoter and a mildly acidic accelerator.

In U.S. Pat. No. 3,816,488, Craddock et al. disclose an improved process for the production of carboxylic acids by the reaction of ethylenically unsaturated compounds with carbon monoxide and water, in the presence of catalyst compositions essentially comprising rhodium compounds and complexes, together with an iodide promoter in critical proportions (I:Rh=3:1 to 200:1) to obtain predominantly linear products.

In U.S. Pat. No. 5,145,995, Burke discloses a process for the preparation of 3-pentenoic acid which comprises reacting in a solvent consisting essentially of at least one carboxylic acid selected from the group of aliphatic $C_2$–$C_{20}$ carboxylic acids, benzoic acid and alkyl-substituted benzoic acids wherein the total number of carbons in the alkyl group(s) is not more than 3: butadiene, carbon monoxide, and water with a rhodium catalyst and a promoter selected from the class consisting of bromide and iodide.

In U.S. Pat. No. 4,645,863, Rebafka et al. disclose a process for the preparation of unsaturated alcohols and/or esters thereof by reacting conjugated dienes with water and/or aqueous lower aliphatic carboxylic acid solutions in the presence of a macroporous acid ion exchanger having an average pore diameter greater than 50 Angstroms, and a polar aprotic solvent.

SUMMARY OF THE INVENTION

The present invention is a process for the preparation of 3-pentenoic acid which comprises reacting butadiene, carbon monoxide, and water in a solvent consisting essentially of at least one carboxylic acid selected from the group of aliphatic $C_2$–$C_{20}$ carboxylic acids, benzoic acid and alkyl-substituted benzoic acids wherein the total number of carbons in the alkyl group(s) is not more than 3 and in the presence of a rhodium catalyst, an iodide promoter, and a heterogeneous or homogeneous sulfonic acid catalyst, at a temperature in the range of about 50° C. to about 110° C. and at a carbon monoxide partial pressure in the range of about 100 to about 1000 psig, wherein the concentration of rhodium is in the range of about 0.005% to about 0.50% by weight of the total weight of the reaction mixture, and the molar ratio of promoter to rhodium is between about 1:1 and about 10:1.

DETAILED DESCRIPTION OF THE INVENTION

In the process of this invention, the rate of conversion of butadiene to 3-pentenoic acid at low temperatures is significantly increased by the use of a dual catalyst system comprising a heterogeneous or homogeneous sulfonic acid and an iodide promoted rhodium catalyst. To obtain the benefits of this dual catalyst system, the water is maintained at a sufficiently high concentration to favor rapid hydration of butadiene to butenyl alcohols and esters, but not so high as to inhibit the rapid carbonylation of these intermediates to 3-pentenoic acid.

Either heterogeneous or homogeneous sulfonic acids may be beneficially employed in the process of this invention. The preferred catalysts are heterogeneous sulfonic acids such as macroporous and microporous ion exchange resins. Highly crosslinked (macroporous) styrene-divinylbenzene based ion exchange resins are most preferred. When a resin sulfonic acid is employed the results will depend on the sulfonic acid content and the strength of the sulfonic acid. With a typical resin containing about 4.7 milli-equivalents of sulfonic acid per gram of resin, best results are obtained when the amount of resin is between 0.1 parts and 0.5 parts per part of solution and preferably between 0.2 and 0.4 parts per part of solution. For homogeneous sulfonic acid catalysts, a suitable concentration is in the range 0.2 to 2.0 and preferably 0.5 to 1.0 milli-equivalents per milliliter of solution. Examples of heterogeneous sulfonic acid catalysts that may be used in the process of this invention include Amberlyst® 15, Amberlyst® XN-1010, Amberlite® IR-118, Amberlite® IR-120(plus), Lewatit® K2611 and Nafion® (acid form of perfluorinated sulfonic acid resin). Examples of homogeneous sulfonic acid catalysts that may be used in the process of this invention include methanesulfonic acid and para-toluenesulfonic acid.

The temperature of the reaction is in the range of about 50° C. to about 120° C. with temperatures between about 80° C. and about 100° C. being preferred. Above about 120° C. the initially formed 3-pentenoic acid is readily lactonized in the presence of the highly acid resin component of the catalyst. Above 130°-140° C. the resin degrades by loss of sulfonic acid groups.

Suitable CO partial pressures are in the range of from about 25 psi to about 1000 psi at reaction temperature. The optimum CO partial pressure will depend on the temperature with higher pressures being required to stabilize the catalyst at higher temperatures. Suitable total pressures are in the range of from about 60 to 400 psi at 80° to 110° C.

The source of the reactants for the present process is not particularly critical. Commercially available grades of carbon monoxide (CO) and butadiene (BD) are satisfactory. The carbon monoxide can contain inert impurities such as carbon dioxide, methane, nitrogen, nobel gases, and paraffinic hydrocarbons having from 1 to 4 carbon atoms. The carbon monoxide can also contain hydrogen. The hydrocarboxylation reaction of this invention requires at least a 1:1 molar ration of CO to BD; however, an excess of CO is generally used.

The amount of unreacted butadiene in the reaction mixture should be controlled such that its concentration is less than 10% of the solution to maintain satisfactory reaction rates. The concentration of butadiene can be controlled by continuous or stepwise addition of BD to the reaction.

Suitable solvents for this process are aliphatic $C_2$–$C_{20}$ monocarboxylic acids, aliphatic $C_4$–$C_{20}$ dicarboxylic acids, benzoic acid, alkyl-substituted benzoic acids wherein the total number of carbon atoms in the alkyl group(s) is not more than 3, and mixtures thereof. The preferred carboxylic acid solvents are aliphatic $C_2$–$C_6$ monocarboxylic acids, $C_4$–$C_7$ dicarboxylic acids, benzoic acid and mixtures thereof. The most preferred monocarboxylic acid solvents are acetic, propionic, butyric, 2-methylbutyric, valeric, and caproic acids and mixtures thereof. Mixtures of monocarboxylic and dicarboxylic acids produced directly or indirectly in the hydrocarboxylation of butadiene can also be used in whole or in part as the solvent for this process. Such monocarboxylic and dicarboxylic acids include, but are not limited to, adipic, valeric, 2-methylglutaric, ethylsuccinic, dimethylsuccinic, and methylbutyric acids. The most preferred solvent, for reasons of economy and convenience in conjunction with the manufacture of adipic acid, is the mixture of monocarboxylic and dicarboxylic acids obtained from the hydrocarboxylation of 3-pentenoic acid after the removal of the bulk of the adipic acid. The reaction mixture may also contain minor amounts of inert solvents such as $C_6$–$C_{10}$ aromatic solvents and $C_5$–$C_{10}$ aliphatic solvents.

Water is necessary for the hydrocarboxylation of butadiene with the dual catalyst system. It can be obtained from water added to the reaction mixture or from water formed under the reaction conditions (for example, from the formation of esters or anhydrides). However, water should not be present in large excess, and is preferably present in an amount between about 3 and 20%, more preferably between 5 and 15%, and most preferably between about 5 and 10%, based on the weight of the reaction mixture. (The weight of the reaction mixture includes the weight of the solvent(s), catalysts, promoter(s) and reactants.) The water can be present in the solution at the beginning of the reaction, or it can be added continuously as it is consumed to avoid undesirably high concentrations.

The optimum water concentration will depend on the amount and type of sulfonic acid used as co-catalyst. Since the resin catalysts (heterogeneous catalysts) will absorb a significant amount of the water initially present in the homogeneous solution phase, higher water concentrations can be tolerated with these catalysts than with homogeneous acids. When larger amounts of resin co-catalyst are employed, both the maximum and minimum water concentration required for adequate reaction rates and yields is higher than for lower resin loadings.

The process of this invention can be run either as a batch or continuous process. When a batch process is employed with an acid ion exchange resin catalyst, at least 5% water should be initially present in order to achieve the desired water concentration since the resin will absorb significant amounts of water from the solution.

The rhodium catalyst can be provided from any source or by any material which will produce rhodium ions under hydrocarboxylation conditions. Among the materials which can be employed as the source of the rhodium catalyst are rhodium metal, rhodium salts, rhodium oxides, rhodium carbonyl compounds, organorhodium compounds, coordination compounds of rhodium and mixtures thereof. Specific examples of such materials include, but are not limited to, rhodium-(III) chloride and its hydrates, $RhI_3$, $Rh(CO)_2I_3$, $Rh(CO)I_3$, rhodium (III) nitrate trihydrate, $Rh_4(CO)_{12}$, $Rh_6(CO)_{16}$, $Rh(acac)_3$, $Rh(CO)_2(acac)$, $Rh(C_2H_4)_2(acac)$, $[Rh(C_2H_4)_2Cl]_2$, $[Rh(CO)_2Cl]_2$, $Rh(COD)(acac)$, $[Rh(COD)Cl]_2$, $RhCl(CO)(PPh_3)_2$, $Rh_2[O_2C(CH_2)_6CH_3]_4$ and $Rh_2(acetate)_4$, where acac is acetylacetonate and COD is 1,5-cyclooctadiene. Supported rhodium compounds, e.g., Rh/C and Rh/alumina, can also be used as a source of the rhodium catalyst. Rhodium compounds containing bidentate phosphine or nitrogen ligands should be avoided. Preferred sources of the rhodium catalyst include rhodium (I) compounds such as $[Rh(CO)_2Cl]_2$, $[Rh(COD)Cl]_2$, and $Rh(COD)(acac)$ and rhodium iodide compounds such as $RhI_3$ and $Rh(CO)_2I_3$.

Suitable concentrations of rhodium are in the range of 0.005–0.50% by weight of rhodium metal based on the weight of the reaction mixture. Preferably, the concentration of rhodium is in the range of 0.01–0.20 wt %, more preferably 0.04–0.10 wt %.

The rhodium catalyst, which can be preformed or formed in situ, must by promoted by HI or compounds which generate HI under the reaction conditions (e.g., acetyl iodide) to achieve high reaction rates and high selectivity to adipic acid and its precursors. Molar ratios of iodide-to-rhodium between about 1 and 10 may be employed. For best results, the molar ratio of iodide-to-rhodium should be between about 2 and 4. Suitable sources of the promoter include HI and iodide salts of rhodium.

In the practice of this invention, efficient mass transfer between the gas and liquid phases is of critical importance in order to minimize catalyst deactivation. Thus, in order to obtain optimum results, it is essential that the reaction mixtures be well mixed.

EXAMPLE 1

A slurry of Amberlyst ® 15 resin (a sulfonated styrene-divinylbenzene macroreticular ion-exchange resin)(dry form, 20 g) in a solution containing glacial acetic acid (42.6 mL), water (7.2 g 400 mmol) and aq HI (57%, 0.18 g, 0.8 mmol HI), was charged into a glass-lined 400 mL shaker tube and $(Rh(CO)_2I)_2$ (0.12 g, 0.4 meq) was added. The tube was closed, cooled to −30° C., evacuated, and 2.7 g (50 mmol) butadiene was added. It was then pressured with carbon monoxide to 500 psi. The tube was heated with agitation to 88° C. over about 40 min; the total pressure at 88° C. was about 686 psi. The temperature was maintained at 88° C. for 3 hrs, after which it was allowed to cool to room temperature. The excess CO pressure and any unreacted butadiene or butenes in the vapor phase were slowly vented, the product was discharged and the tube was rinsed with acetic acid (2×50 mL). The product and washings were combined, o-dichlorobenzene (2.0 g, internal standard) was added and the solution was made up to 200 mL with acetic acid. Part of the solution was analyzed directly by GC for butenyl alcohols and butenyl acetate derivatives on a 30 m×0.25 mm "DBFFAP" capillary GC column. A second portion of the solution was esterified with methanol BF3 reagent and analyzed as the methyl esters on a 30 m×0.25 mm "CP-Wax-57" CB capillary GC column. The results are summarized in Table 1.

COMPARATIVE EXAMPLE 1A

The procedure described in Example 1 was repeated, except that the Amberlyst ® resin was omitted. The results are shown in Table 1.

COMPARATIVE EXAMPLE 1B

The procedure described in Example 1 was repeated, except that the Amberlyst ® resin was omitted, the amount of water was reduced to 3.0% (1.4 g, 77 mmol), and the amount of acetic acid was increased to 44.4 mL. The results are shown in Table 1.

TABLE 1

|  | Expt. 1 | Expt. 1A | Expt. 1B |
|---|---|---|---|
| % Water | 14.4 | 14.4 | 3.0 |
| g Amberlyst ® 15/100 ml | 40 | 0 | 0 |
| PRODUCTS (Moles per 100 moles Butadiene charged) |  |  |  |
| Butenyl Acetates* | 1.1 | 0.5 | 1.1 |
| 3-Pentenoic Acid | 71.9 | 2.0 | 46.1 |
| gamma-Valerolactone | 3.7 | 0.0 | 0.0 |

*The butenyl acetates consisted of a mixture of 3-buten-2-ol acetate and 2-buten-1-ol acetate (crotyl acetate).

The data show that addition of the Amberlyst resin to the Rh catalyst in a solution containing 15% water leads to a large increase in 3-pentenoic acid yield when compared with the control containing the same HI/Rh ratio but without the resin co-catalyst (Expt. 1A). The results of Example 1 are also superior to those obtained using a much lower amount of water (Expt. 1B) in the absence of the resin co-catalyst. The results of Comparative Example 1B illustrate that the beneficial result obtained in Example 1 is not simply the result of water being removed from the reaction system by absorption into the resin.

EXAMPLES 2 and 3

The experiment in Example 1 was repeated except that the mount of water was varied. The results obtained are summarized in Table 2.

TABLE 2

|  | Ex. 2 | Ex. 3 |
|---|---|---|
| % Water | 5 | 10 |
| g Amberlyst ® 15/100 ml | 40 | 40 |
| Temperature | 88 | 88 |
| PRODUCTS (Moles per 100 moles Butadiene charged) |  |  |
| Butenyl Derivatives* | 1.1 | 0.6 |
| 3-Pentenoic Acid | 54.5 | 71.3 |
| gamma-Valerolactone | 6.9 | 2.7 |

*The butenyl derivatives consisted of a mixture of 3-buten-2-ol acetate, 3-buten-2-ol, 2-buten-1-ol acetate (cis- and trans-crotyl acetate) and 2-buten-1-ol (cis- and trans-crotyl alcohol). Typically the ratios of these compounds were, in order, 5:2.2:9.1:1.0

The data shows that the conversion of butadiene to 3-pentenoic is higher at 10% water and that the yield of gamma-Valerolactone decreases with water concentration.

EXAMPLES 4 and 5

The experiment in Example 1 was repeated except that the water concentration was 10% and the temperature was varied. The results obtained are summarized in Table 3.

TABLE 3

|  | Expt. 4 | Expt. 5 |
|---|---|---|
| % Water | 10 | 10 |
| g Amberlyst ® 15/100 ml | 40 | 40 |
| Temperature | 110 | 130 |
| PRODUCTS (Moles per 100 moles Butadiene charged) |  |  |
| Crotyl esters | 1.1 | 0.6 |
| 3-Pentenoic Acid | 38.4 | 1.7 |
| gamma-Valerolactone | 0.9 | 27.2 |

The data shows that the conversion of butadiene to 3-pentenoic acid decreases and the concentration of valerolactone increases as the temperature is increased.

EXAMPLES 6-8

The experiment in Example 1 was repeated except that the acid catalyst was varied and the water concentration was maintained at 10%. The results are summarized in Table 4.

TABLE 4

| Ex. | Acid | Amount (g/100 ml) | Moles/100 Moles BD Butenols | 3PA | VL |
|---|---|---|---|---|---|
| 6 | Lewatit ® -K2611* | 40 | 1.0 | 87.3 | 4.9 |
| 7 | Amberlite ® (plus)** | 40 | 3.0 | 60.8 | 2.3 |
| 8 | Nafion ® (H+)*** | 40 | 3.9 | 41.1 | 3.5 |

*A strongly acidic, macroreticular ion-exchange resin which can be generically described as a sulfonated styrene-divinylbenzene polymer.
**A strongly acidic, gel type ion-exchange resin. The resin is a microporous sulfonated styrene-divinylbenzene polymer.
***A super acidic, microporous ion-exchange resin. This resin is a perfluorinated sulfonic acid.

The results show that a variety of strong acid catalysts will promote the rhodium catalysed hydrocarboxylation of butadiene.

EXAMPLE 9

Amberlyst ® 15 (3.0 g) was charged to a 90 ml capacity Fisher-Porter tube which was then purged with carbon monoxide containing 5% hydrogen. A CO/H$_2$ (95:5) sparged acetic acid solution (15 ml) containing butadiene (5.8%), water (5.0%) and o-dichlorobenzene (internal GC standard; 1.0%), was cooled to about 10° C. and added to the Fisher-Porter tube by vacuum suction. Rhodium dicarbonyl diiodide-HI catalyst (0.09 meq Rh, I/Rh ratio 4.0) in 3:1 acetic acid-water (0.42 g) was then added in a similar manner. The light brown solution was pressured with 95:5 CO/H$_2$ to 100 psi at 25° C., heated to 90° C. and maintained at 90° C. for 7 hours. Liquid samples were taken at intervals via a dip leg to determine the kinetics of the carbonylation. Table 5 summarizes the course of the reaction with time.

TABLE 5

| Moles Compound per 100 Moles BD charged | | | | |
|---|---|---|---|---|
| time (min) | BD | sec-Butyl Acetate | Butenyl Acetates* | 3PA + VL** |
| 0 | 99.2 | 0.0 | 0.8 | 0.0 |
| 5 | 95.4 | 0.0 | 5.0 | 2.0 |
| 15 | 65.0 | 0.0 | 15.6 | 5.7 |
| 30 | 50.2 | 0.0 | 32.3 | 14.3 |
| 60 | 28.2 | 0.0 | 37.0 | 28.5 |
| 120 | 13.5 | 1.0 | 25.8 | 58.0 |
| 240 | 5.2 | 2.9 | 8.8 | 72.2 |
| 360 | 2.0 | 4.7 | 2.5 | 75.5 |

*A mixture of 3-buten-2-ol acetate and 2-buten-1-ol acetate (crotyl acetate)
**The ratio of 3PA to VL in final (360 minute) sample was 5.6

The results indicate that butenyl acetates are formed initially and that these compounds are subsequently irreversibly converted to 3-pentenoic acid. Based on these data, the initial rate of 3PA formation was 0.008 min−1 and the time for 50% conversion to 3PA was about 86 minutes.

EXAMPLES 10-15

The experiment in Example 9 was repeated except that the amount of water was varied from 10% to 0% and the initial butadiene concentration was different. The results are shown in Table 6.

TABLE 6

| Ex. | % BD | % Water added | % Conv to 3PA + VL (2 Hrs) | Rate (min-1) |
|---|---|---|---|---|
| 10 | 5.3 | 1.0 | 39 | 0.0047 |
| 11 | 8.0 | 7.5 | 37 | 0.0041 |
| 12 | 5.3 | 5.0 | 60 | 0.0075 |
| 13 | 6.5 | 3.75 | 31 | 0.0107 |
| 14 | 6.1 | 2.5 | 14 | 0.0063 |
| 15 | 6.1 | 0.0 | 2.9 | 0.0009 |

The data show that water concentration is important. For the amount of resin used in these examples (20 g/100 ml) the optimum water concentration is about 5%; the yield of 3PA+VL falls off at higher and lower water concentrations. There is extensive oligomerization of the butadiene in the absence of water.

EXAMPLES 16 AND 17

The experiment in Example 12 was repeated except that the amount of HI was varied to vary the I/Rh ratio. The results are summarized in Table 7.

TABLE 7

| Ex. | I/Rh | % Water added | % Conv to 3PA + VL (2 Hrs) | Rate (min-1) |
|---|---|---|---|---|
| 16 | 2.0 | 5.0 | 64.4 | 0.0087 |
| 17 | 6.0 | 5.0 | 35.0 | 0.0039 |

The results show that the catalyst activity varies with the I/Rh ratio; higher activities are obtained at the lower ratios.

EXAMPLES 18-21A

The experiment in Example 9 was repeated except that the ion exchange resin was replaced with a homogeneous acid, the initial BD concentration was about 5.2% and the water concentration was varied. A control experiment (Example 21 A) was run under similar conditions, but without acid co-catalyst. The results obtained are shown in Table 8.

TABLE 8

| Ex. | Acid Catalyst (meq H+/100 meq BD) | % BD | % Water | % Conv to 3PA + VL (2 Hrs) | (min1) |
|---|---|---|---|---|---|
| 18 | p-TSA* (93) | 5.2 | 3.6 | 52.3 | 0.0061 |
| 19 | p-TSA (93) | 5.2 | 1.5 | 57.1 | 0.011 |
| 20 | MSA** (93) | 5.2 | 1.5 | 65.6 | 0.011 |
| 21 | MSA (46) | 5.2 | 1.5 | 51.5 | 0.006 |
| 21A | NONE | 4.7 | 1.7 | 41.7 | 0.0046 |

*p-TSA = p-toluenesulfonic acid hydrate
**MSA = methanesulfonic acid

The results show that homogeneous acids will also accelerate the carbonylation of butadiene to 3-PA.

I claim:

1. A process for the preparation of 3-pentenoic acid which comprises forming a reaction mixture of: butadiene; carbon monoxide; water in the amount of 1 to 20 percent by weight of the reaction mixture; a carboxylic acid solvent selected from the group of aliphatic $C_2$–$C_{20}$ carboxylic acids, benzoic acid and alkyl-substituted benzoic acids wherein the total number of carbons in the alkyl group(s) is not more than 3; a homogeneous rhodium catalyst; a heterogeneous or homogeneous sulfonic acid catalyst; and an iodide promoter and reacting said mixture at a carbon monoxide partial pressure in the range of about 50 to 1000 psi, and at a temperature of about 50° to 120° C.

2. The process of claim 1 in which the promoter is hydrogen iodide and the molar ratio of iodide-to-rhodium is between 1 and 10.

3. The process of claim 1 wherein the rhodium is present in the reaction mixture in the amount of at least 0.1 part by weight per 1000 parts by weight of the reaction mixture.

4. The process in claim 1 wherein the sulfonic acid catalyst is heterogeneous and is an ion exchange resin containing sulfonic acid groups.

5. The process in claim 1 wherein the sulfonic acid catalyst is heterogeneous and is a macroporous ion exchange resin based on a sulfonated styrene-divinylbenzene copolymer containing between 8 and 20% divinylbenzene.

6. The process in claim 1 wherein the sulfonic acid catalyst is homogeneous and is methanesulfonic acid.

7. The process in claim 1 wherein the sulfonic acid catalyst is homogeneous and is para-toluenesulfonic acid.

* * * * *